United States Patent [19]
Roussis et al.

[11] Patent Number: 5,808,180
[45] Date of Patent: *Sep. 15, 1998

[54] DIRECT METHOD FOR DETERMINATION OF TRUE BOILING POINT DISTILLATION PROFILES OF CRUDE OILS BY GAS CHROMATOGRAPHY/MASS SPECTROMETRY

[75] Inventors: Stilianos G. Roussis, Brights Grove; James W. Fedora; William P. Fitzgerald, both of Sarnia, all of Canada

[73] Assignee: Exxon Research and Engineering Company, Florham Park, N.J.

[*] Notice: The term of this patent shall not extend beyond the expiration date of Pat. Nos. 5,600,134, 5,699,269 and 5,602,755.

[21] Appl. No.: 711,621

[22] Filed: Sep. 12, 1996

[51] Int. Cl.$^6$ .................................................... G01N 30/02
[52] U.S. Cl. .......................................... 73/23.35; 73/61.44
[58] Field of Search .............................. 73/19.02, 23.35, 73/23.37, 23.38, 23.41, 25.01, 61.43, 61.44, 61.52; 208/80; 436/161, 60

[56] References Cited

U.S. PATENT DOCUMENTS

| | | | |
|---|---|---|---|
| 4,631,687 | 12/1986 | Kowalski et al. | 73/61.52 |
| 5,119,315 | 6/1992 | Kemp et al. | 364/498 |
| 5,121,377 | 6/1992 | Brown | 364/498 |
| 5,218,529 | 6/1993 | Meyer et al. | 364/413 |
| 5,446,681 | 8/1995 | Gethner et al. | 364/554 |
| 5,600,134 | 2/1997 | Ashe et al. | 250/252.1 |
| 5,602,755 | 2/1997 | Ashe et al. | 364/498 |
| 5,699,269 | 12/1997 | Ashe et al. | 364/499 |

FOREIGN PATENT DOCUMENTS 3-100463  4/1991  Japan ......................................... 33/22

OTHER PUBLICATIONS

George, G.N.; & Gorbaty, M.L.; Sulfur K–Edge X–ray Absorption Spectroscopy of Petroleum Asphaltenes and Model Compounds; Journal of the American Chemical Society, 1989, III, pp. 3182–3186.

Butler R.D.; Chromatography in Petroleum Analysis; Chapter 4, Simulated Distillation by Gas Chromatography; Marcel Dekker: New York, 1979; pp. 75–89.

Eggersten, F.T.; Groennings, S.; & Holst, J.J.; Analytical Distillation by Gas Chromatography; Analytical Chemistry, vol. 32, No. 8, Jul. 1960, pp. 904–909.

Green, L.E.; Schmauch, L.J.; & Worman, J.C.; Simulated Distillation by Gas Chromatography; Analytical Chemistry, vol. 36, No. 8, Jul. 1964, pp. 1512–1516.

*Primary Examiner*—Hezron E. Williams
*Assistant Examiner*—Jay L. Politzer
*Attorney, Agent, or Firm*—James H. Takemoto

[57] ABSTRACT

This invention relates to a method for rapidly determining weight and volume percent true boiling point curves for crude oils and fractions thereof. The method involves at least a partial separation of the crude oil or fraction into constituent chemical components, obtaining mass spectra of the chemical components, correlating retention time windows with boiling points for standard hydrocarbon mixtures, and converting the total ion current obtained from the mass spectra for selected components to weight and volume percent true boiling points by comparison with data obtained from a standard crude oil or fraction thereof.

5 Claims, 6 Drawing Sheets

DIRECT METHOD FOR DETERMINATION OF TRUE BOILING POINT DISTILLATION PROFILES OF CRUDE OILS BY GAS CHROMATOGRAPHY/MASS SPECTROMETRY

FIELD OF THE INVENTION

This invention relates to the use of gas chromatographic distillation/mass spectrometry for the determination of the weight and liquid volume percent true boiling point curves for crude oils and fractions thereof, and correlation thereof with molecular information.

DESCRIPTION OF THE RELATED ART

Determination of the true boiling point curve for crude oil is an important measurement used for decisions concerning control of refinery processes. Small variations in the true boiling point curve may have a significant impact on process control and overall profitability. Therefore, utilization of reliable standard methods able to provide accurate and precise true boiling point (tBP) curves is very important to the petroleum industry.

Standard distillation methods are specified by the American Society for Testing and Materials (ASTM). ASTM methods D-2892 and D-5236 cover physical distillation procedures for crude oils and heavy hydrocarbon fractions. These physical distillation methods can generate tBP curves as well as individual boiling point fractions which can be used for further chemical and physical testing (crude assay). These physical methods require more than 0.5L of sample, take up to 2 or more days for experimental completion and are subject to variables such as operator skill. Upon acquisition of a crude oil % yield as a function of boiling point, further mathematical treatment is required to generate a single tBP curve.

Another approach to obtain tBP information is Gas Chromatographic Simulated Distillation (GC SIMDIS or GCD). The use of gas chromatography to simulate physical distillation of petroleum samples is well known in the art, e.g., Butler, Chromatography in Petroleum Analysis, Altgelt and Gouw eds, Marcel Dekker, N.Y. 1979, pp. 75–99. ASTM methods have been developed which describe the procedures for GC SIMDIS gasoline (D-3710), petroleum fractions (D-2887) and whole crudes (D-5307).

It would be desirable to have a method for determining tBP curves of petroleum samples while simultaneously obtaining information about molecular composition at different boiling range intervals.

SUMMARY OF THE INVENTION

This invention relates to a process for determining weight and volume percent true boiling point curves for crude oils and fractions thereof using molecular composition information obtained from a mass spectrometer which comprises:

(1) introducing the crude oil or fraction thereof into a gas chromatograph or other means for separating the crude oil or fraction thereof based on boiling points thereby causing at least a partial separation of the crude oil or fraction thereof into constituent chemical components as a function of retention time;

(2) introducing the constituent chemical components into a mass spectrometer;

(3) obtaining a series of time resolved mass chromatograms;

(4) selecting a series of retention time windows;

(5) converting the retention time windows to their corresponding boiling points by comparing retention time windows to boiling curves derived from standard hydrocarbon mixtures;

(6) obtaining a total ion current from a summation of the accumulated signal of the mass spectra of the crude oil or fraction thereof for the selected time windows;

(7) converting the total ion current for the selected time windows to weight % true boiling point by comparison with a corresponding true boiling point amount for the selected time windows obtained from a standard crude oil or fraction thereof;

(8) selecting characteristic mass ions within the selected retention time windows, said characteristic mass ions identifying chemical composition within the selected retention time windows; and (9) converting the weight % true boiling point to volume % true boiling point based on the known densities for chemical constituents of the chemical composition for the selected retention time windows.

DETAILED DESCRIPTION OF THE INVENTION

Figure 1:
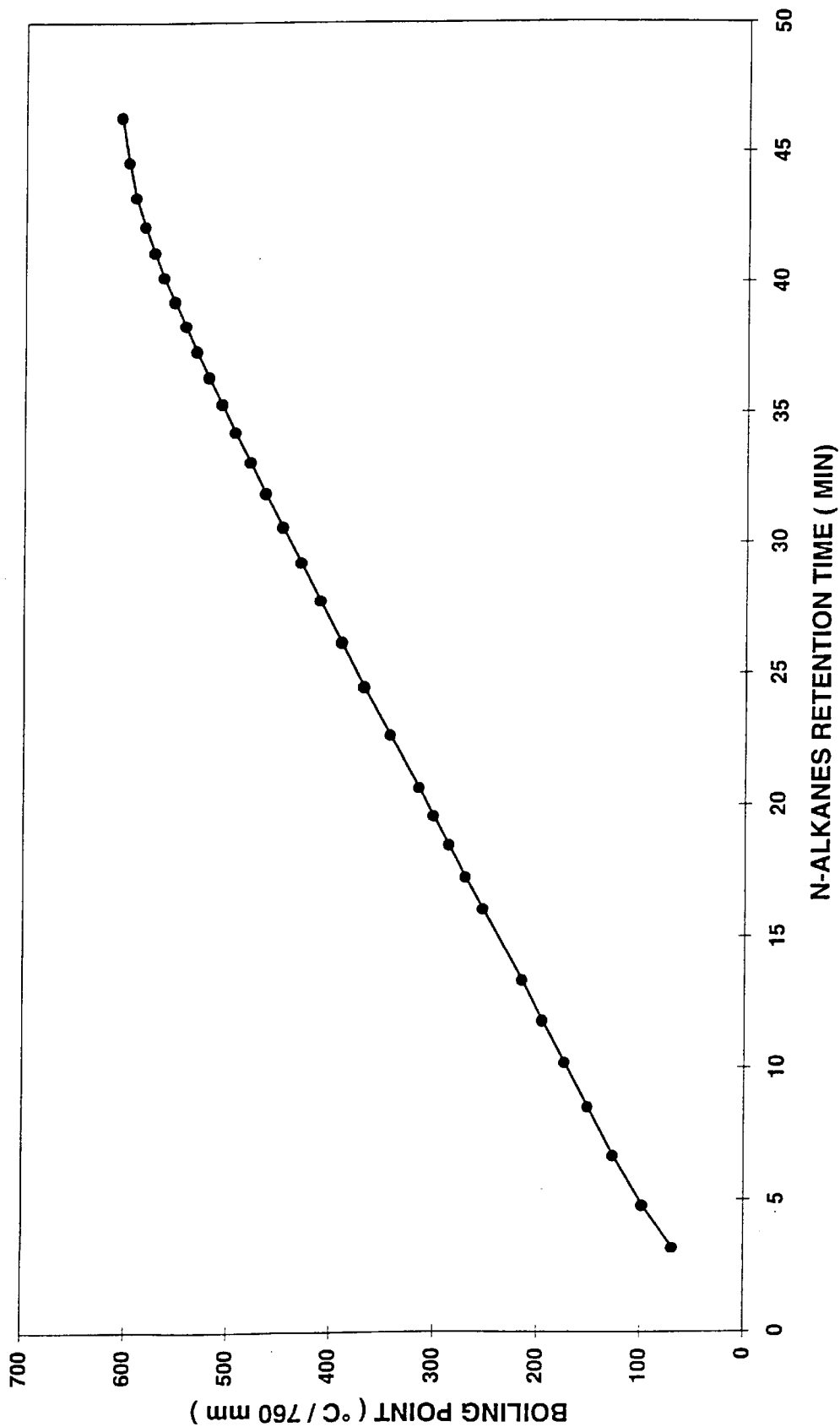
FIG. 1 is a graph showing a plot the retention times of known alkanes vs. boiling point.

This invention provides a method for obtaining both weight and volume percent true boiling point (tBP) curves for crude oils and fractions thereof together with information on the chemical composition of the crude oils and fractions as a function of boiling point. This method has the advantage of providing the above-noted information in a single measurement in a short period of time as compared to conventional methods for obtaining this information. These advantages are obtained by using a combination of gas chromatographic distillation coupled with a mass spectrometer. The method can be fully automated and can yield wt. % and vol. % tBP curves within 1 hour or less.

While a gas chromatograph is the preferred means for separating crude oils or fractions thereof into constituent chemical components, other means for accomplishing the same purpose may be used, such as direct insertion probe, heated inlet, supercritical fluid chromatography, liquid chromatography, size exclusion chromatography, distillation and the like may be used. The use of gas chromatographs for such purposes is well known in the art. Capillary gas chromatographs are especially preferred.

In the mass spectrometer, sample molecules are bombarded with high energy electrons thereby creating molecular ions which fragment in a pattern characteristic of the molecular species involved. A continuous series of mass spectra are obtained over a scan range of about 10 to 800 Daltons. The mass spectral data may also be acquired in selected ion monitoring mode. In this mode, care must be taken to select ions representative of the components of interest and to operate under repeatable conditions. A variety of mass spectrometers may be used including low resolution, high resolution, MS/MS, ion cyclotron resonance and time of flight. Any ionization technique may be used such as electron ionization, chemical ionization, multiphotonionization, field desorpion, field ionization and the like, provided that the technique provides either molecular or fragment ions which are suitable for use in the present method.

The sample to be analyzed is first injected into a GC where the sample components are separated as a function of retention time and boiling point. Only partial chromatographic resolution of sample components is necessary. Components may also be identified by a detector such as a flame ionization detector, thermal conductivity detector, atomic emission detector or electron capture detector.

The separated or partially separated components are then transferred to a mass spectrometer (MS). The transfer may be accomplished with a mass spectrometer which is directly interfaced with the gas chromatograph or may be accomplished indirectly by injecting the components separately. If the mass spectrometer is interfaced with the gas chromatograph, the transfer will normally take place under dynamic flow conditions. A series of mass spectra are obtained for the separated or partially separated components based on their differing retention times.

The conversion of the gas chromatographic retention time scale to the boiling point scale can be accomplished using standard mixtures of n-alkanes as designated by ASTM D-2887 or D-5307. An analysis of n-alkylaromatic compounds of the same carbon numbers showed that the n-alkylaromatics do not elute at the same rate as n-alkanes. This may result in slight differences in assigned boiling points for material boiling within a given retention time interval depending on whether one uses the n-alkane or n-alkylaromatic with the same carbon numbers. However, the overall approach using gas chromatographic distillation (GCD) is acceptable.

Based on the retention time windows selected, one obtains a total ion current (TIC) which is a summation of the accumulated signal of the mass spectra within the selected time windows. One TIC is generated for each crude mass chromatogram (spectra). The complete mass spectral array may typically consist of 6,000 or more individual mass spectra. This data set is reduced by an order of magnitude by the summation of mass spectra which are characteristic of the hydrocarbon types expected within any given retention time window. Thus 6,000 mass spectra can be reduced to about 600 mass spectra. In order to convert the TIC to a weight % tBP curve for the set of retention time windows, a comparison is made with a similar TIC analysis for a standard crude, e.g., Arab light. The standard crude has a known weight percent boiling point distribution as a function of retention time. By comparing the known boiling point (BP) distribution with the TIC, one obtains a series of coefficients for the selected time windows. These coefficients are then used to calculate the weight percent for the unknown sample based on the corresponding TIC's for the standard crude vs. the unknown crude as shown in the following equation.

$$\text{wt. \% of } BP \text{ window} = \frac{TIC \text{ of crude for } BP \text{ window}}{TIC \text{ of standard crude for } BP \text{ window}} \times$$

wt. % of standard crude for $BP$ window

For each selected retention time window, one selects mass ions which are characteristic of compounds expected within that retention time window. A typical crude analysis may yield 6,000 or more mass spectra each of which creates a data point in the overall mass chromatogram. By employing an averaging procedure, the number of mass spectra can be reduced about 10 fold which results in about 600 mass spectra. These individual mass spectra provide a unique molecular diagnostic for chemical composition of the crude.

Because of the complexity of hydrocarbon compounds within any given crude, it is preferred to use hydrocarbon type analysis in order to reduce the data to a manageable set. While the selection of appropriate hydrocarbon types may vary according to the sample under investigation, a typical set might include, paraffins, 1- to 3- ring cycloparaffins, alkylbenzenes, mono- and dinaphthenebenzenes, naphthalenes, acenaphthenes/dibenzofurans, fluorenes, phenanthrenes, naphthenephenanthrenes, pyrenes, chrysenes, perylenes, dibenzanthracenes, benzo- and dibenzothiophenes, naphtobenzothiophenes and the like. Each of the hydrocarbon types produces characteristic mass ions which can be used as diagnostics for the hydrocarbon type. Thus for each retention time window, a set of diagnostic mass ions is selected for the hydrocarbon types expected within that retention time window. This then provides data on the actual chemical composition within the selected time window. Once the compositional data are known, the densities of the different chemical compounds can be readily determined. These densities are then applied to the weight percent tBP curve obtained above to yield a volume percent tBP curve.

Thus by using the method according to the invention, one can determine the wt. % tBP, the vol. % tBP together with compositional information on the crude or fraction thereof in a single experiment. Since the GC and MS utilize computer software for data acquisition and data reduction, the process can be fully automated.

The method of the invention is further illustrated by the following examples.

EXAMPLE 1

The experimental procedure is described in this example. The sample to be analyzed is injected into a GC through a cold, vacuum-tight non-discriminating injector that can he heated at a rapid, controllable rate. Such injection systems may be obtained e.g., from Gerstel (Germany). It is important to introduce the entire sample without discrimination and simultaneously maintain vacuum-tight seals. Otherwise, an incorrect analysis may result. The samples may be diluted with solvent and are typically introduced using an autosampler.

A Hewlett-Packard 5890 Series II gas chromatograph containing a short, non-polar capillary column is used for the GC analysis. Typical parameters include: 15 m fused silica capillary column with 0.25 mm i.d. and 0.1 $\mu$m film thickness; programmed oven from −40° C. to 380° C. at 10° C./min.

The mass spectrometer which is interfaced with the GC is a Hewlett-Packard 5970 quadrupole mass spectrometer. The interface temperature is 300° C. The mass spectrometer is operated in the full scan mode from 10 to 800 Daltons at a scanning rate of 1 sec/scan and is tuned in the Electron Ionization mode using perfluorotertbutylamine as a marker.

EXAMPLE 2

This example demonstrates the use of a calibration curve obtained from a standard hydrocarbon mixture. The boiling points for the known hydrocarbons in the mixture is plotted against retention times obtained by GCD analysis using the procedure from example 1. The results are shown in FIG. 1 which is a plot of boiling point vs. retention time. When an unknown sample is examined by the procedure of example 1 to obtain retention times, the retention times are converted to their corresponding boiling points by correlation with the calibration curve. A 5th order polynomial equation is used for curve fitting of the data points in the boiling point calibration curve. The experimental data are used to determine the coefficients of the equation. Boiling point assignment for unknowns is then done for unknown samples using the 5th order equation. A different order polynomial equation can also be used. Other mathematical curve-fitting or interpolation routines can be used for the calibration.

EXAMPLE 3

Figure 2:
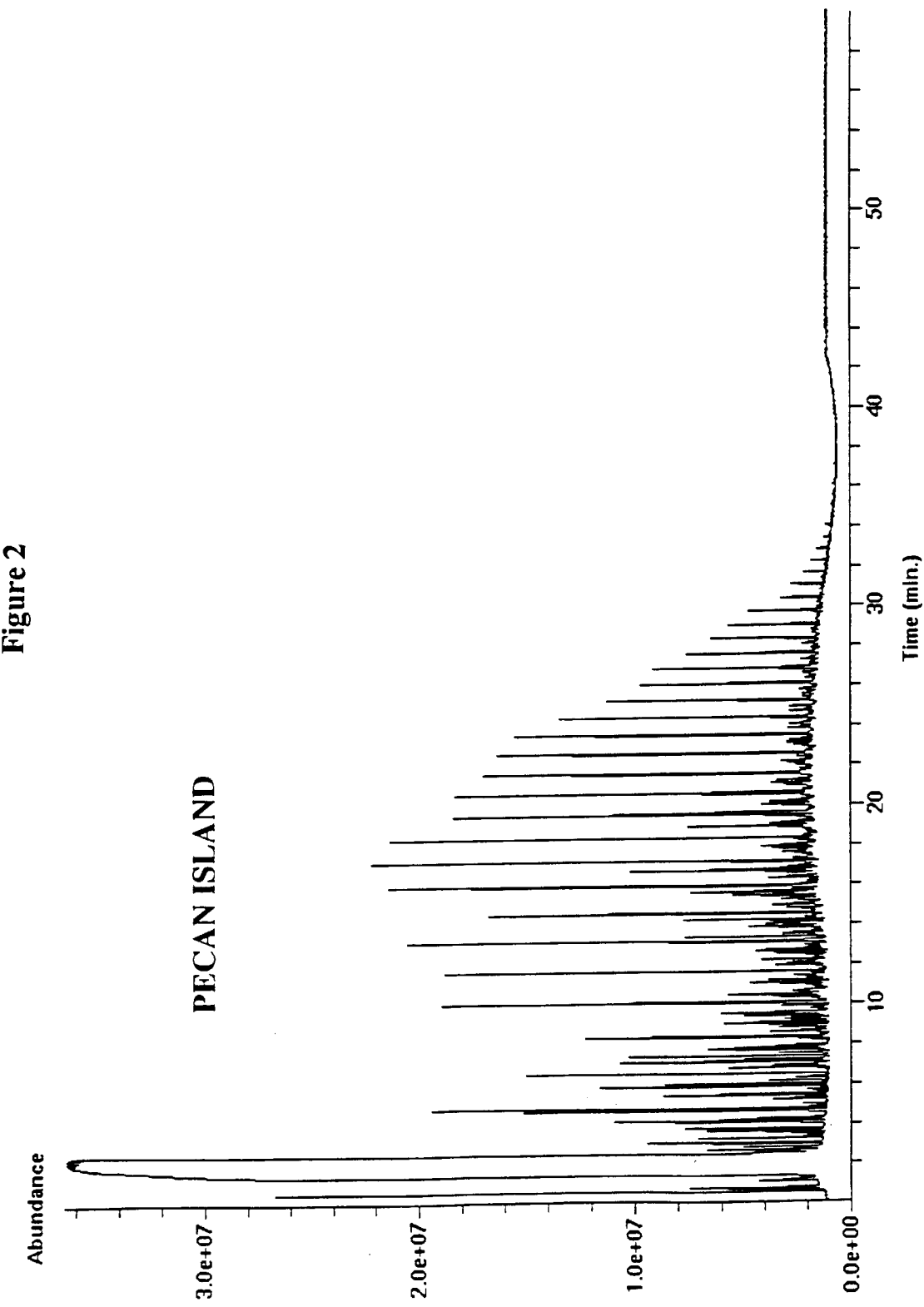
FIG. 2 is a graph showing ion abundance as a function of retention time for a Pecan Island crude oil.

The total ion current (TIC) for crudes are demonstrated in this example. Five crudes are examined by GCD/MS technology with Arab light as the external calibrant. FIG. 2 is a graph of the raw TIC for Pecan Island crude. The x-axis is the retention time axis in minutes and the y-axis is the ion abundance scale in area counts. Each data point in the chromatogram is reconstructed from the summation of the ion signal of all masses in the scan. About 6,000 data points are included in the chromatogram. The mass chromatogram for this particular crude is contained in a 6,000×790 data array. In order to reduce the total amount of data, a summation procedure is performed which results in about 600 mass spectra. These mass spectra provide unique molecular fingerprints of the chemical composition of the analyzed crude.

EXAMPLE 4

The use of hydrocarbon chemical type analysis to reduce the data set is illustrated in this example. As shown in example 3, there are a large number of raw mass spectra generated which would require several hours of computer time for analysis. In order to reduce the data to a manageable set, the data is correlated to conventional hydrocarbon chemical types as a function of boiling point. This type of data presentation reduces the mass axis in the data matrix from 790 to 25. Furthermore, the 600 boiling point data set were reduced to the standard crude assays boiling point fractions (20). An example of the chemical types for Pecan Island Crude is shown in Table 1.

TABLE 1

| | | | | | | | | | | | | | | | | | | | |
|---|---|---|---|---|---|---|---|---|---|---|---|---|---|---|---|---|---|---|---|
| Avg. boiling pt. (deg c) | 100 | 125 | 150 | 175 | 205 | 220 | 235 | 265 | 295 | 318.89 | 343.33 | 398.89 | 426.67 | 454.44 | 482.22 | 510 | 537.78 | 565 | 593.33 |
| Avg. retention time (min) | 4.25 | 5.55 | 7.35 | 9.2 | 11.25 | 12.95 | 14.05 | 15.65 | 17.85 | 19.85 | 21.6 | 24.6 | 27.75 | 29.85 | 32 | 34.2 | 36.4 | 38.65 | 41.15 |
| Weight Percent | 5.66 | 4.6 | 5.09 | 6.64 | 7.05 | 3.99 | 4.79 | 10.06 | 9.35 | 7.6 | 5.72 | 10.03 | 3.39 | 2.37 | 1.53 | 0.94 | 0.54 | 0.33 | 0.37 |
| Paraffins | 2.2 | 0.9 | 1.5 | 2.1 | 2.2 | 1.8 | 0.9 | 3.2 | 3.2 | 2.8 | 1.3 | 2.5 | 0.6 | 0.2 | 0.0 | 0.0 | 0.0 | 0.0 | 0.0 |
| 1-ring cycloparaffins | 0.7 | 1.3 | 1.0 | 0.9 | 1.1 | 0.6 | 0.9 | 1.9 | 1.8 | 1.6 | 1.2 | 2.1 | 0.7 | 0.4 | 0.3 | 0.1 | 0.0 | 0.0 | 0.0 |
| 2-ring cycloparaffins | 0.2 | 0.0 | 0.1 | 0.4 | 0.6 | 0.3 | 0.3 | 0.9 | 0.8 | 0.6 | 0.7 | 1.2 | 0.4 | 0.3 | 0.2 | 0.1 | 0.0 | 0.0 | 0.0 |
| 3-ring cycloparaffins | 0.9 | 0.9 | 0.8 | 0.7 | 1.1 | 0.6 | 0.8 | 1.7 | 1.3 | 1.1 | 1.1 | 1.8 | 0.8 | 0.6 | 0.5 | 0.3 | 0.2 | 0.1 | 0.1 |
| Alkylbenzenes | 0.3 | 0.7 | 1.0 | 1.0 | 1.0 | 0.3 | 0.2 | 0.5 | 0.4 | 0.3 | 0.3 | 0.4 | 0.1 | 0.1 | 0.0 | 0.0 | 0.0 | 0.0 | 0.0 |
| Naphthenebenzenes | 0.4 | 0.1 | 0.2 | 0.2 | 0.3 | 0.2 | 0.2 | 0.5 | 0.4 | 0.3 | 0.2 | 0.4 | 0.1 | 0.2 | 0.1 | 0.1 | 0.1 | 0.1 | 0.1 |
| Dinaphthenebenzenes | 0.2 | 0.3 | 0.3 | 0.3 | 0.4 | 0.2 | 0.2 | 0.5 | 0.6 | 0.4 | 0.3 | 0.5 | 0.2 | 0.1 | 0.1 | 0.1 | 0.0 | 0.0 | 0.0 |
| Naphthalenes | 0.2 | 0.0 | 0.0 | 0.1 | 0.2 | 0.1 | 0.4 | 0.7 | 0.6 | 0.3 | 0.2 | 0.3 | 0.1 | 0.1 | 0.0 | 0.0 | 0.0 | 0.0 | 0.0 |
| Acenaphthenes/Dibenzofura | 0.0 | 0.0 | 0.0 | 0.0 | 0.1 | 0.0 | 0.0 | 0.0 | 0.1 | 0.1 | 0.1 | 0.1 | 0.1 | 0.1 | 0.1 | 0.0 | 0.1 | 0.1 | 0.1 |
| Fluorenes | 0.0 | 0.0 | 0.0 | 0.0 | 0.0 | 0.0 | 0.0 | 0.0 | 0.0 | 0.0 | 0.1 | 0.2 | 0.1 | 0.1 | 0.1 | 0.0 | 0.1 | 0.1 | 0.0 |
| Phenanthrenes | 0.0 | 0.0 | 0.0 | 0.0 | 0.0 | 0.0 | 0.0 | 0.0 | 0.0 | 0.0 | 0.0 | 0.1 | 0.0 | 0.0 | 0.0 | 0.0 | 0.0 | 0.0 | 0.0 |
| Naphthenephenanthrenes | 0.0 | 0.0 | 0.0 | 0.0 | 0.0 | 0.0 | 0.0 | 0.0 | 0.0 | 0.0 | 0.1 | 0.1 | 0.1 | 0.1 | 0.1 | 0.0 | 0.1 | 0.1 | 0.1 |
| Pyrenes | 0.0 | 0.0 | 0.0 | 0.0 | 0.0 | 0.0 | 0.0 | 0.0 | 0.0 | 0.0 | 0.0 | 0.2 | 0.0 | 0.0 | 0.0 | 0.0 | 0.0 | 0.0 | 0.0 |
| Chrysenes | 0.0 | 0.0 | 0.0 | 0.0 | 0.0 | 0.0 | 0.0 | 0.0 | 0.0 | 0.0 | 0.0 | 0.1 | 0.0 | 0.0 | 0.0 | 0.0 | 0.0 | 0.0 | 0.0 |
| Perylenes | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Dibenzanthracenes | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Benzothiophenes | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Dibenzothiophenes | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Naphthobenzothiophenes | 0.0 | 0.1 | 0.0 | 0.0 | 0.0 | 0.0 | 0.0 | 0.0 | 0.1 | 0.0 | 0.0 | 0.0 | 0.0 | 0.0 | 0.0 | 0.0 | 0.0 | 0.0 | 0.0 |
| Cn.H2n-36/Cn.H2n-26.S | 0.0 | 0.1 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Cn.H2n-38/Cn.H2n-28.S | 0.3 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Cn.H2n-26 | 0.1 | 0.2 | 0.1 | 0.0 | 0.0 | 0.0 | 0.0 | 0.0 | 0.0 | 0.0 | 0.0 | 0.0 | 0.0 | 0.0 | 0.0 | 0.0 | 0.1 | 0.1 | 0.1 |
| Cn.H2n-42/Cn.H2n-32.S | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Cn.H2n-44/Cn.H2n-34.S | 0.1 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Cn.H2n-32 | 0.1 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Total Saturates | 4.0 | 3.1 | 3.5 | 4.1 | 5.1 | 3.3 | 3.8 | 7.7 | 7.1 | 6.1 | 4.2 | 7.6 | 2.5 | 1.6 | 0.9 | 0.5 | 0.3 | 0.1 | 0.1 |
| Monoaromatics | 0.9 | 1.0 | 1.5 | 1.4 | 1.7 | 0.6 | 0.6 | 1.5 | 1.4 | 0.9 | 0.9 | 1.3 | 0.4 | 0.3 | 0.2 | 0.2 | 0.1 | 0.0 | 0.0 |
| Diaromatics | 0.2 | 0.0 | 0.0 | 0.1 | 0.3 | 0.1 | 0.4 | 0.8 | 0.6 | 0.4 | 0.4 | 0.6 | 0.2 | 0.2 | 0.1 | 0.1 | 0.1 | 0.1 | 0.2 |
| Triaromatics | 0.0 | 0.0 | 0.0 | 0.0 | 0.0 | 0.0 | 0.0 | 0.0 | 0.0 | 0.0 | 0.0 | 0.2 | 0.0 | 0.1 | 0.1 | 0.0 | 0.0 | 0.0 | 0.0 |
| Tetraaromatics | 0.0 | 0.1 | 0.0 | 0.0 | 0.0 | 0.0 | 0.0 | 0.0 | 0.1 | 0.1 | 0.1 | 0.2 | 0.1 | 0.0 | 0.0 | 0.0 | 0.1 | 0.1 | 0.1 |
| Pentaaromatics | 0.0 | 0.0 | 0.0 | 0.0 | 0.0 | 0.0 | 0.0 | 0.0 | 0.0 | 0.0 | 0.0 | 0.1 | 0.1 | 0.0 | 0.0 | 0.0 | 0.0 | 0.0 | 0.0 |
| Thiophenoaromstics | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 | 0.0 |
| Unidentified Aromatics | 0.5 | 0.4 | 0.1 | 0.1 | 0.0 | 0.0 | 0.0 | 0.1 | 0.1 | 0.0 | 0.0 | 0.0 | 0.0 | 0.1 | 0.1 | 0.1 | 0.1 | 0.1 | 0.1 |
| Total Aromatics | 1.6 | 1.5 | 1.6 | 1.6 | 2.0 | 0.7 | 1.0 | 2.4 | 2.3 | 1.5 | 1.5 | 2.5 | 0.9 | 0.8 | 0.6 | 0.4 | 0.3 | 0.2 | 0.3 |

Figure 3:
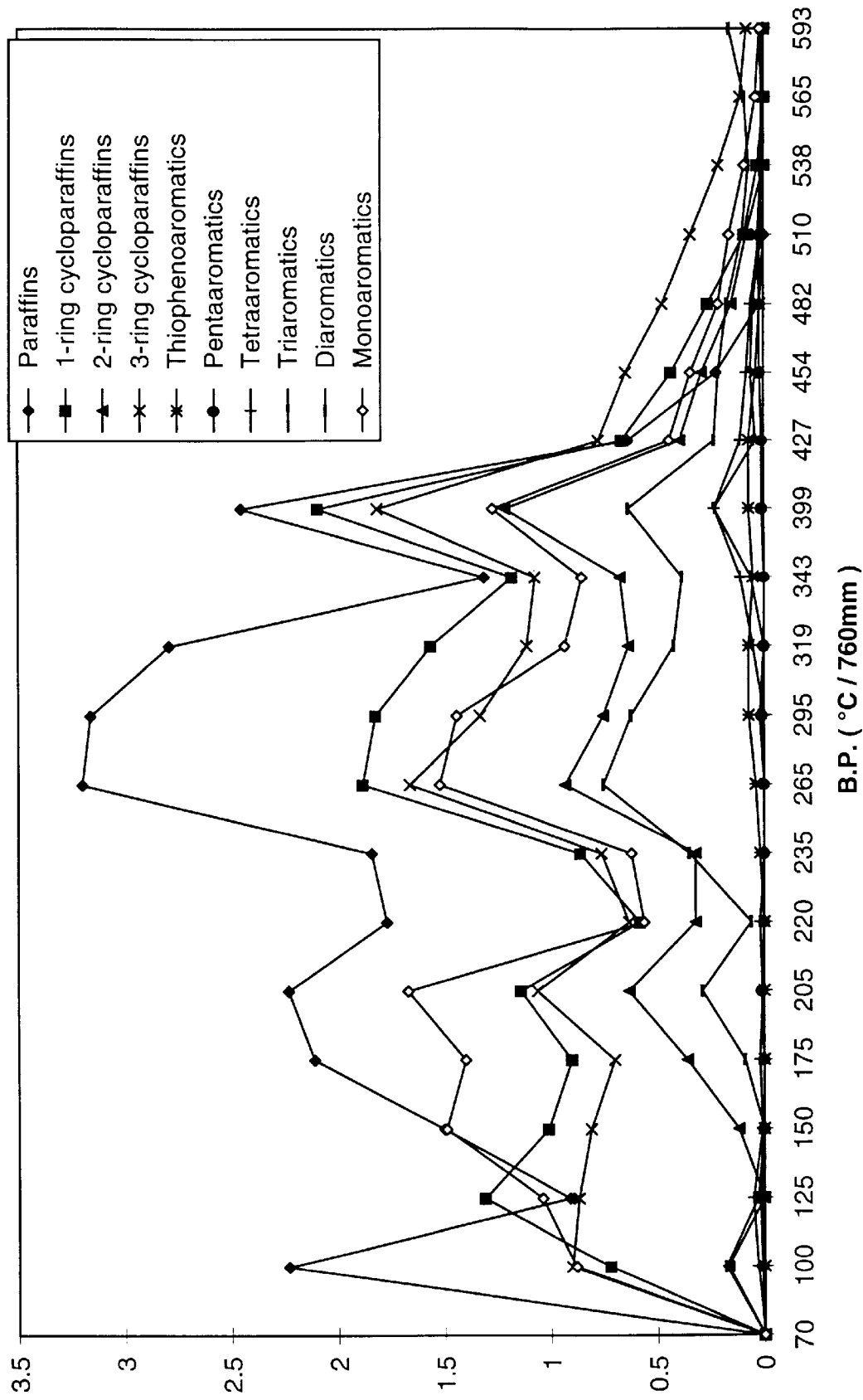
FIG. 3 is a graph of hydrocarbon type analysis as a function of retention time for a Pecan Island crude oil.
Figure 4:
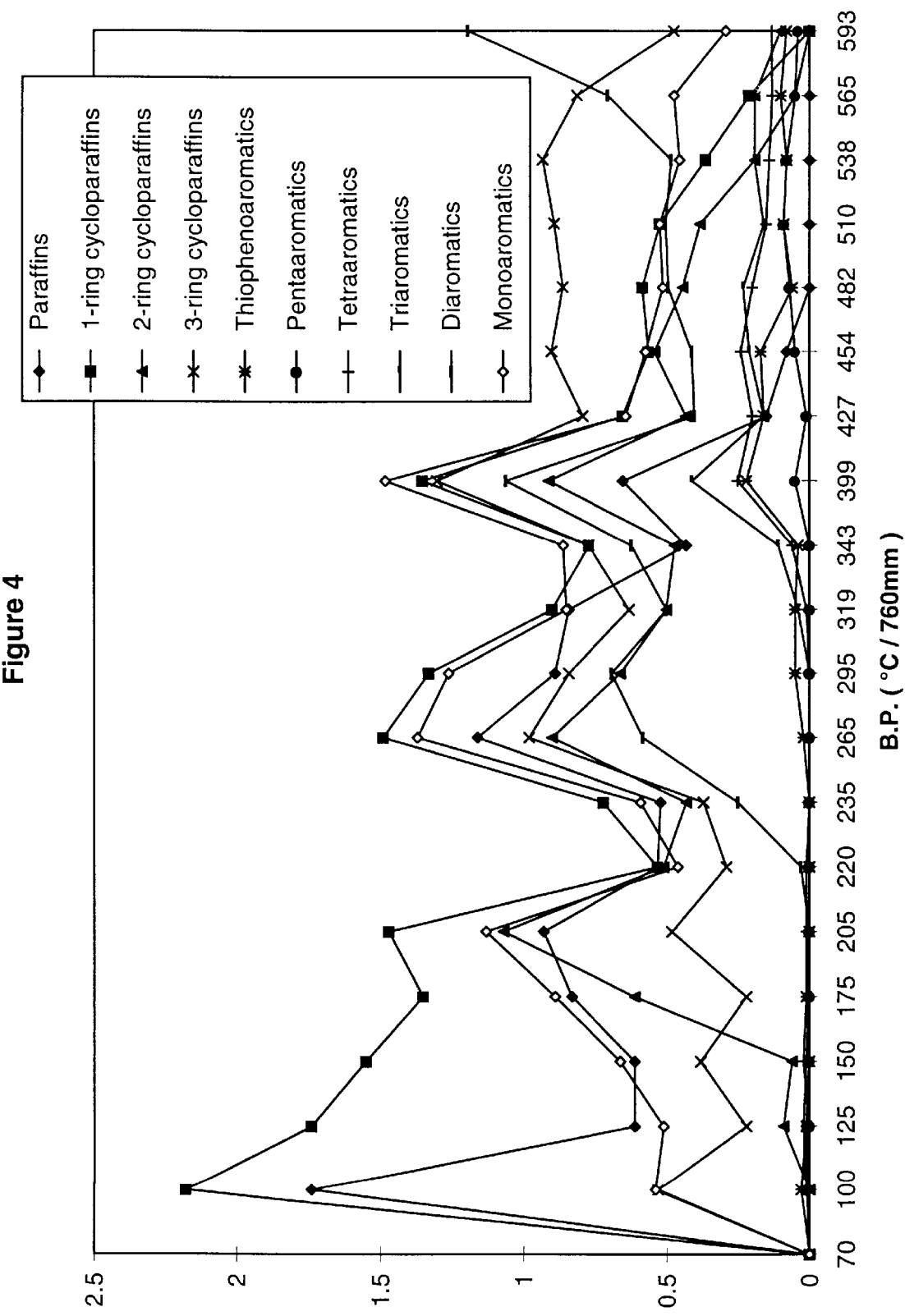
FIG. 4 is a graph of hydrocarbon type analysis as a function of retention time for a Duc crude oil.

This table present the weight % chemical types distribution as a function of boiling points. The chemical types data are produced by standard mass spectrometric techniques that allow the conversion of the raw data to hydrocarbon types data. These conversion methods are based on the quantitative analysis of individual components in the complex mixture using known linear algebraic mathematical methods. This type of GCD/MS chemical types analysis provides the total amounts of compounds in the same chemical class. Further breakdowns within any given class can be obtained using external or internal calibration procedures with known amounts of standard compounds. The results of a hydrocarbon chemical types analysis is shown in FIGS. 3 and 4 which are graphs of Pecan Island Crude and Duc crude. These figures show the differences in chemical composition between the two crudes. A total of ten different hydrocarbon types are shown for purposes of simplicity of illustration.

EXAMPLE 5

This example shows the wt. % and vol. % tBP curves for Pecan Island Crude obtained from the GCD/MS analysis. The wt. % tBP curve for Pecan Island Crude is determined by comparison of the TIC obtained from the GCD/MS analysis with physical distillation data (as a function of retention time) for a known standard such as Arab Light. Table 2 is a calibration summary for Arab Light.

TABLE 2

EXTERNAL STANDARD CALIBRATION SUMMARY

| CUT TEMP (°C.) | | PHYS. DIST. WT. % OF STANDARD CRUDE (ARAB LT) | | |
|---|---|---|---|---|
| IBP | FBP | INITIAL YIELD | WEIGHT YIELD | FINAL YIELD |
| 37 | 70 | 1.10 | 2.47 | 3.57 |
| 71 | 100 | 3.63 | 3.24 | 6.87 |
| 101 | 125 | 6.94 | 3.14 | 10.08 |
| 126 | 150 | 10.16 | 3.60 | 13.76 |
| 151 | 175 | 13.85 | 4.07 | 17.92 |
| 176 | 205 | 18.02 | 5.26 | 23.28 |
| 206 | 220 | 23.38 | 2.62 | 26.00 |
| 221 | 235 | 26.11 | 2.66 | 28.77 |

TABLE 2-continued

EXTERNAL STANDARD CALIBRATION SUMMARY

| CUT TEMP (°C.) | | PHYS. DIST. WT. % OF STANDARD CRUDE (ARAB LT) | | |
|---|---|---|---|---|
| IBP | FBP | INITIAL YIELD | WEIGHT YIELD | FINAL YIELD |
| 236 | 265 | 28.87 | 5.51 | 34.39 |
| 266 | 295 | 34.49 | 5.59 | 40.08 |
| 296 | 319 | 40.18 | 4.27 | 44.45 |
| 319 | 343 | 44.55 | 4.17 | 48.72 |
| 344 | 399 | 48.81 | 8.58 | 57.39 |
| 399 | 427 | 57.47 | 3.87 | 61.34 |
| 427 | 454 | 61.42 | 3.74 | 65.16 |
| 455 | 482 | 65.23 | 3.61 | 68.84 |
| 483 | 510 | 68.91 | 3.55 | 72.47 |
| 511 | 538 | 72.54 | 3.48 | 76.02 |
| 538 | 565 | 76.09 | 3.39 | 79.48 |

Figure 5:
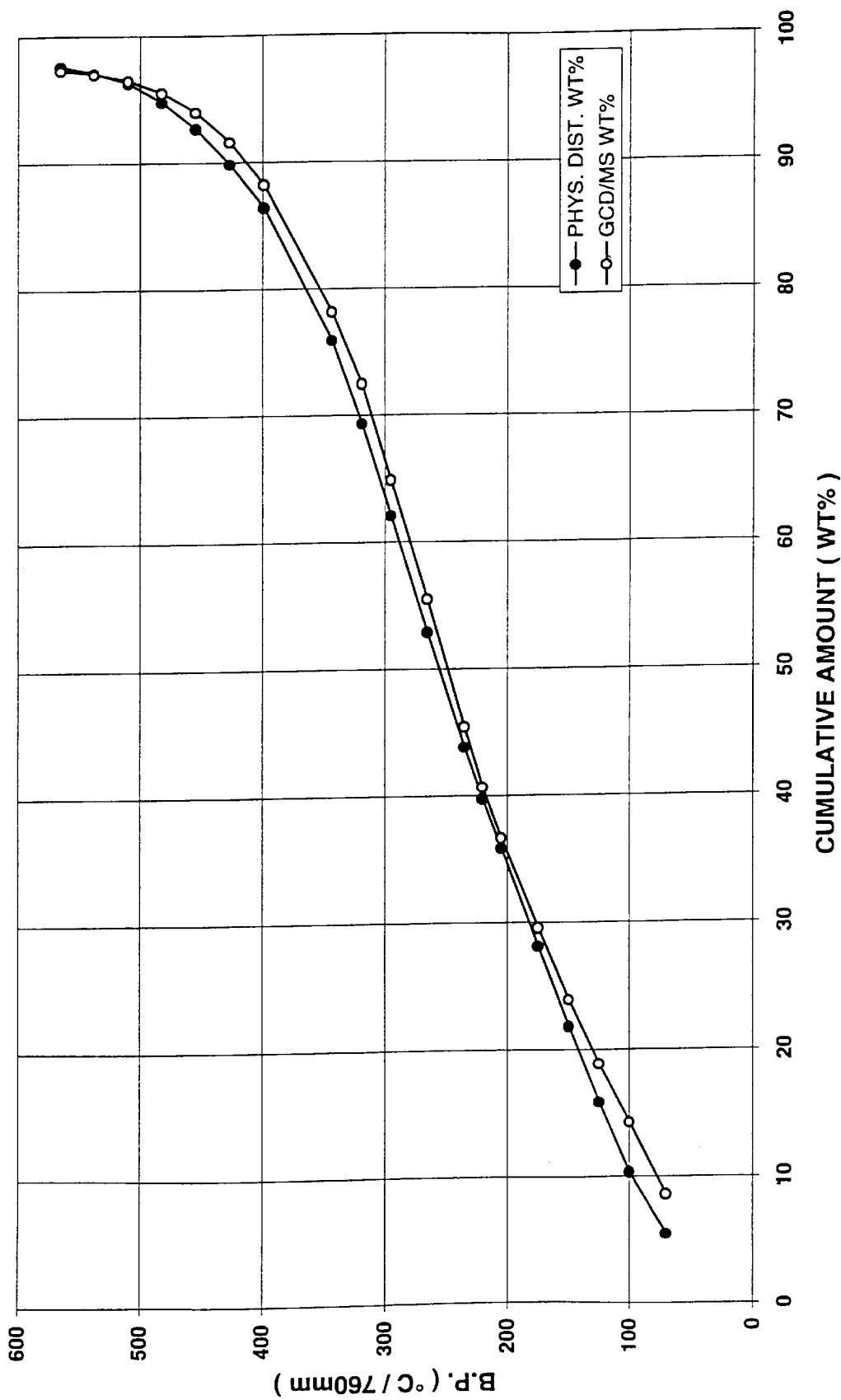
FIG. 5 is a graph showing cumulative weight % vs. boiling point for a Pecan Island crude oil obtained by actual physical distillation and by GCD/MS.
Figure 6:
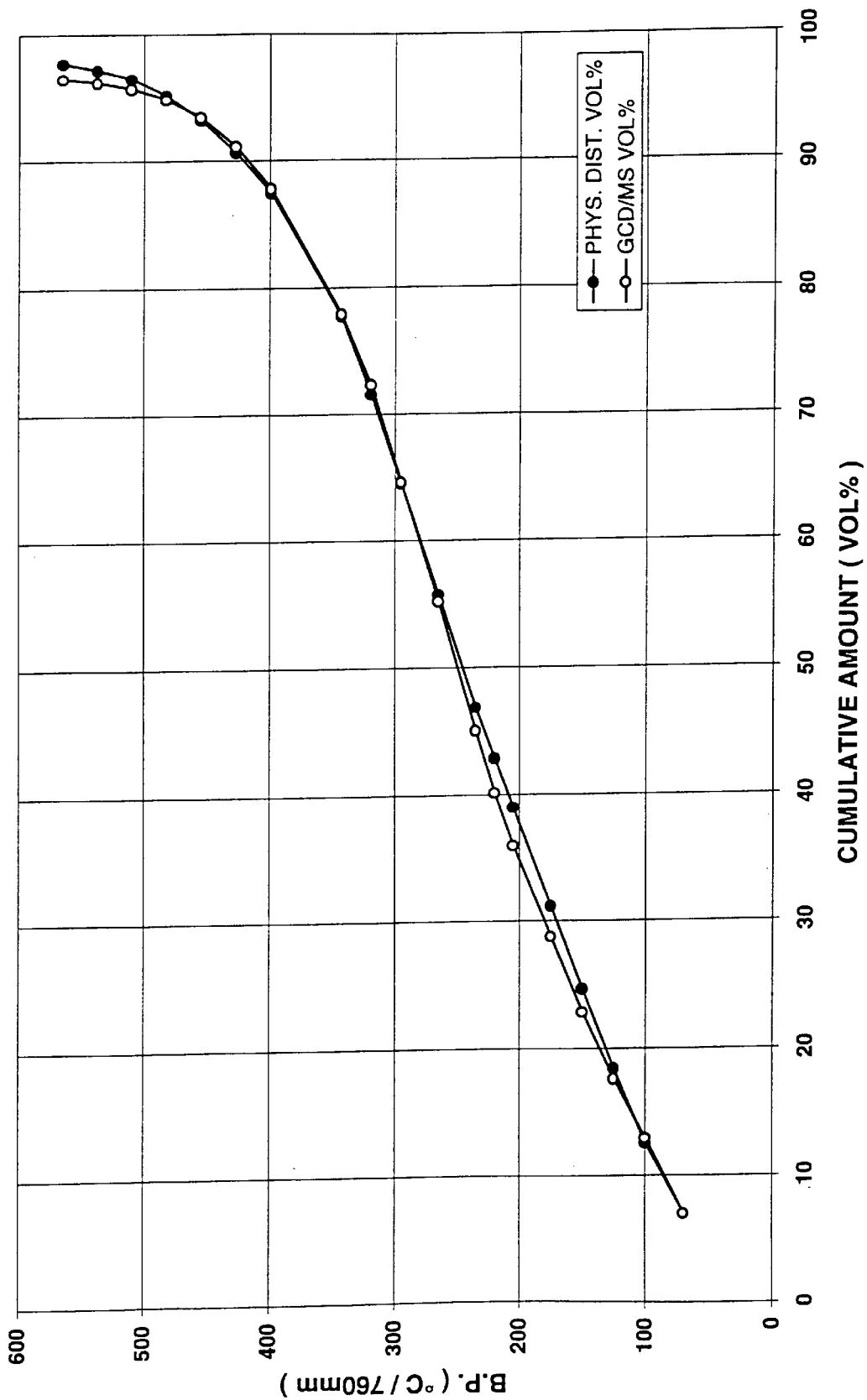
FIG. 6 is a graph showing cumulative volume % vs. boiling point for a Pecan Island crude oil obtained by actual physical distillation and by GCD/MS.

FIG. 5 is a graph showing cumulative weight % vs. boiling point obtained from actual physical distillation and GCD/MS analysis. FIG. 6 is a graph showing cumulative vol. % vs. boiling point obtained from actual physical distillation and GCD/MS analysis. The GCD/MS volume points were determined from knowing the hydrocarbon types as a function of retention time. By using the densities of the known hydrocarbon types (which can be obtained from standard reference tables) and the wt. % as a function of boiling point (see FIG. 5), one can convert to vol. % using the following equations:

vol. % of chemical component in $BP$ window =

$$\frac{\text{wt. \% of } BP \text{ window}}{\text{density of chemical component in } BP \text{ window}} \times \frac{\text{density of whole crude}}{\text{(fraction)}}$$

Total vol. % in $BP$ window =

Sum of vol. % of individual chemical components $BP$ window

As can be seen from FIGS. 5 and 6, there is good agreement between actual physical distillation data and the results obtained from GCD/MS analysis.

EXAMPLE 6

The procedure of Example 5 was repeated for five other crudes. Tables 3 and 4 show the physical distillation and GCD/MS wt. and vol. % for Brunei, Murban, Medanitos, Cabinda and Miandoum crudes.

TABLE 3

COMPARISON OF PHYSICAL DISTILLATION AND GCD/MS WT. % DATA FOR 5 CRUDES

| | CUMULATIVE AMOUNT WEIGHT % | | | | | | | | | |
|---|---|---|---|---|---|---|---|---|---|---|
| BOILING | BRUNEI LT | | MURBAN | | MEDANITOS | | CABINDA | | MIANDOUM 3TE3 | |
| POINT (°C.) | PHYS DIST | GCD.MS | PHYS DIST | GCD.MS | PHYS DIST | GCD.MS | PHYS DIST | GCD.MS | PHYS DIST | GCD.MS |
| 70 | 4.27 | 4.33 | 6.30 | 5.97 | 2.88 | 3.33 | 3.99 | 3.41 | 0.33 | 0.50 |
| 100 | 10.05 | 10.06 | 10.79 | 10.93 | 7.18 | 7.51 | 6.89 | 6.17 | 0.56 | 0.50 |
| 125 | 18.77 | 20.82 | 15.28 | 15.87 | 11.28 | 12.09 | 9.56 | 9.09 | 0.86 | 0.70 |
| 150 | 26.41 | 27.08 | 20.51 | 20.99 | 15.53 | 16.00 | 12.45 | 11.87 | 1.20 | 0.92 |
| 175 | 33.15 | 33.37 | 26.28 | 26.40 | 19.92 | 19.70 | 15.61 | 14.79 | 1.65 | 1.44 |
| 205 | 41.04 | 41.40 | 33.06 | 33.10 | 25.34 | 25.26 | 19.77 | 18.53 | 2.95 | 2.96 |
| 220 | 45.46 | 45.35 | 36.37 | 36.37 | 28.11 | 28.06 | 22.00 | 20.63 | 4.13 | 4.05 |
| 235 | 50.34 | 49.99 | 39.69 | 39.91 | 30.91 | 31.13 | 24.30 | 23.17 | 5.67 | 5.41 |
| 265 | 60.14 | 61.46 | 46.31 | 46.53 | 36.57 | 37.49 | 29.07 | 28.21 | 9.18 | 9.69 |
| 295 | 69.81 | 70.55 | 52.53 | 53.07 | 42.26 | 43.56 | 33.93 | 33.05 | 13.24 | 14.41 |
| 319 | 75.92 | 77.53 | 57.33 | 58.00 | 46.99 | 48.54 | 38.00 | 37.36 | 16.93 | 18.14 |
| 343 | 80.70 | 82.20 | 61.75 | 62.67 | 51.64 | 52.96 | 42.09 | 41.34 | 20.85 | 22.51 |
| 399 | 88.36 | 89.76 | 70.21 | 71.76 | 61.22 | 61.59 | 50.87 | 49.78 | 30.47 | 31.91 |
| 427 | 91.16 | 92.89 | 73.62 | 75.78 | 65.18 | 65.53 | 54.70 | 54.16 | 34.92 | 36.22 |

TABLE 3-continued

COMPARISON OF PHYSICAL DISTILLATION AND GCD/MS WT. % DATA FOR 5 CRUDES

| BOILING | CUMULATIVE AMOUNT WEIGHT % | | | | | | | | | |
|---|---|---|---|---|---|---|---|---|---|---|
| | BRUNEI LT | | MURBAN | | MEDANITOS | | CABINDA | | MIANDOUM 3TE3 | |
| POINT (°C.) | PHYS DIST | GCD.MS | PHYS DIST | GCD.MS | PHYS DIST | GCD.MS | PHYS DIST | GCD.MS | PHYS DIST | GCD.MS |
| 454 | 94.18 | 95.92 | 77.49 | 79.49 | 69.57 | 69.29 | 59.20 | 58.79 | 40.20 | 41.23 |
| 482 | 96.00 | 97.63 | 80.54 | 83.02 | 72.96 | 72.88 | 62.84 | 63.13 | 44.62 | 45.74 |
| 510 | 97.44 | 98.43 | 84.06 | 86.28 | 76.76 | 76.48 | 67.13 | 67.33 | 49.97 | 51.14 |
| 538 | 98.48 | 98.99 | 87.42 | 89.26 | 80.29 | 79.94 | 71.30 | 71.41 | 55.31 | 55.86 |
| 565 | 99.04 | 99.48 | 90.18 | 91.96 | 82.97 | 83.18 | 74.72 | 75.18 | 59.72 | 59.76 |

TABLE 4

COMPARISON OF PHYSICAL DISTILLATION AND GCD/MS WT. % DATA FOR 5 CRUDES

| BOILING | CUMULATIVE AMOUNT WEIGHT % | | | | | | | | | |
|---|---|---|---|---|---|---|---|---|---|---|
| | BRUNEI LT | | MURBAN | | MEDANITOS | | CABINDA | | MIANDOUM 3TE3 | |
| POINT (°C.) | PHYS DIST | GCD.MS | PHYS DIST | GCD.MS | PHYS DIST | GCD.MS | PHYS DIST | GCD.MS | PHYS DIST | GCD.MS |
| 70 | 5.53 | 5.61 | 8.21 | 7.77 | 3.78 | 4.48 | 5.44 | 4.63 | 0.42 | 0.71 |
| 100 | 12.00 | 11.93 | 13.43 | 13.42 | 8.92 | 9.23 | 8.94 | 7.79 | 0.69 | 0.71 |
| 125 | 21.45 | 23.21 | 18.47 | 18.71 | 13.62 | 14.33 | 12.05 | 11.00 | 1.03 | 0.92 |
| 150 | 29.52 | 29.69 | 24.17 | 24.16 | 18.39 | 18.62 | 15.33 | 14.05 | 1.41 | 1.16 |
| 175 | 36.50 | 36.19 | 30.31 | 29.94 | 23.20 | 22.66 | 18.86 | 17.27 | 1.90 | 1.72 |
| 205 | 44.47 | 44.31 | 37.40 | 36.89 | 29.01 | 28.58 | 23.37 | 21.25 | 3.30 | 3.31 |
| 220 | 48.87 | 48.29 | 40.82 | 40.29 | 31.92 | 31.57 | 25.74 | 23.49 | 4.55 | 4.45 |
| 235 | 53.67 | 52.86 | 44.18 | 43.85 | 34.84 | 34.78 | 28.16 | 26.15 | 6.17 | 5.87 |
| 265 | 63.16 | 64.03 | 50.80 | 50.51 | 40.66 | 41.35 | 33.12 | 31.40 | 8.81 | 10.31 |
| 295 | 72.45 | 72.78 | 56.94 | 56.97 | 46.46 | 47.58 | 38.13 | 36.42 | 13.97 | 15.18 |
| 319 | 78.31 | 79.65 | 61.60 | 61.79 | 51.23 | 52.68 | 42.29 | 40.86 | 17.72 | 19.02 |
| 343 | 82.81 | 84.13 | 65.81 | 66.22 | 55.84 | 57.11 | 46.38 | 44.90 | 21.68 | 23.46 |
| 399 | 89.84 | 91.31 | 73.70 | 74.78 | 65.10 | 65.67 | 54.99 | 53.42 | 31.31 | 33.04 |
| 427 | 92.37 | 94.28 | 76.86 | 78.55 | 68.86 | 69.54 | 58.71 | 57.83 | 35.77 | 37.41 |
| 454 | 95.05 | 97.09 | 80.42 | 81.97 | 73.02 | 73.19 | 63.04 | 62.42 | 41.08 | 42.51 |
| 482 | 96.67 | 98.67 | 83.20 | 85.18 | 76.22 | 76.67 | 66.52 | 66.67 | 45.52 | 47.13 |
| 510 | 97.92 | 99.39 | 86.37 | 88.12 | 79.77 | 80.14 | 70.58 | 70.77 | 50.91 | 52.68 |
| 538 | 98.79 | 99.90 | 89.38 | 90.78 | 83.04 | 83.41 | 74.50 | 74.72 | 56.29 | 57.48 |
| 565 | 99.25 | 100.30 | 91.82 | 93.18 | 85.51 | 86.50 | 77.69 | 78.30 | 60.74 | 61.44 |

As can be seen from these tables, there is excellent correlation between the physical distillation data and the GCD/MS data over a range of different crudes.

What is claimed is:

1. A process for determining weight and volume percent true boiling point curves for crude oils and fractions thereof using molecular composition information obtained from a mass spectrometer which comprises:

(1) introducing a sample of crude oil or fraction thereof into a gas chromatograph or other means for separating the crude oil or fraction thereof based on boiling points through a cold, vacuum-tight non-discriminating injector that can be heated at a rapid, controllable rate whereby the entire sample is introduced simultaneously under vacuum-tight seals and without discrimination thereby causing at least a partial separation of the crude oil or fraction thereof into constituent chemical components as a function of retention time;

(2) introducing the constituent chemical components into a mass spectrometer;

(3) obtaining a series of time resolved mass chromatograms over a scan range of about 10 to 800 Daltons;

(4) selecting a series of retention time windows;

(5) converting the retention time windows to their corresponding boiling points by comparing retention time windows to boiling curves derived from standard hydrocarbon mixtures;

(6) obtaining a total ion current from a summation of the accumulated signal of the mass spectra of the crude oil or fraction thereof for the selected time windows;

(7) converting the total ion current for the selected time windows to weight % true boiling point by comparison with a corresponding true boiling point amount for the selected time windows obtained from a standard crude oil or fraction thereof;

(8) selecting characteristic mass ions within the selected retention time windows, said characteristic mass ions identifying chemical composition within the selected retention time windows; and (9) converting the weight % true boiling point to volume % true boiling point based on the known densities for chemical components of the chemical composition for the selected retention time windows.

2. The process of claim 1 wherein the means for separating the crude oil or fraction thereof is a gas chromatograph.

3. The process of claim 1 wherein the summation is based on hydrocarbon type analysis.

4. The process of claim 1 wherein the gas chromatograph is directly interfaced with the mass spectrometer.

5. The process of claim 4 wherein the introduction of step (2) occurs under dynamic flow conditions.

* * * * *